United States Patent
Tsaur

(10) Patent No.: US 6,395,690 B1
(45) Date of Patent: May 28, 2002

(54) PROCESS FOR MAKING MILD MOISTURIZING LIQUIDS CONTAINING LARGE OIL DROPLET

(75) Inventor: Liang Sheng Tsaur, Norwood, NJ (US)

(73) Assignee: Unilever Home & Personal Care USA division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/796,150

(22) Filed: Feb. 28, 2001

(51) Int. Cl.⁷ .................................................. A61K 7/50
(52) U.S. Cl. .................... 510/130; 510/159; 510/497
(58) Field of Search .................... 510/130, 159, 510/473, 474, 417

(56) References Cited

U.S. PATENT DOCUMENTS

| | | |
|---|---|---|
| 5,308,526 A | 5/1994 | Dias et al. |
| 5,441,730 A | 8/1995 | Gough et al. |
| 5,580,550 A | 12/1996 | Gough et al. |
| 5,661,189 A * | 8/1997 | Grieveson et al. .......... 514/784 |
| 5,716,920 A | 2/1998 | Glenn, Jr. et al. |
| 5,854,293 A | 12/1998 | Glenn, Jr. |
| 5,869,070 A | 2/1999 | Dixon et al. |
| 6,066,608 A * | 5/2000 | Glenn, Jr. .................... 510/159 |

FOREIGN PATENT DOCUMENTS

| | | |
|---|---|---|
| EP | 648111 | 4/1995 |
| WO | 96/02224 | 2/1996 |
| WO | 96/17591 | 6/1996 |
| WO | 99/09948 | 3/1999 |
| WO | 99/09950 | 3/1999 |

OTHER PUBLICATIONS

Tsaur et al., 09/796,151, Feb. 28, 2001, Personal Wash Compositions Containing Particle–In–Oil Dispersion.

* cited by examiner

*Primary Examiner*—Necholus Ogden
(74) *Attorney, Agent, or Firm*—Ronald A. Koatz

(57) ABSTRACT

The invention provides a process for making cleansing compositions having desirable moisturization properties by preparing structured liquid base, separately mixing oil and optional polymer to form mixture, mixing or injecting this mixture into the structured base and passing resulting composition through screen with openings larger than 30 micrometer.

5 Claims, No Drawings

PROCESS FOR MAKING MILD MOISTURIZING LIQUIDS CONTAINING LARGE OIL DROPLET

FIELD OF THE INVENTION

The present invention relates to process for making liquid cleansers having large size droplets (i.e., >20 microns, preferably >50 microns). The process comprises passing a composition containing oil or oil/polymer blend through a screen or screens having openings of varying size.

BACKGROUND

Both the rinsing and after-wash skin sensation a product has on the skin can be perceived by many consumers. In many parts of the world, notably China, Japan and other parts of Asia, a soap-like rinsing property (e.g., soap-like "draggy" feeling) is perceived as being thoroughly cleansing and is highly preferred. Soft, smooth, moisturized after-wash skin feel is highly desirable and also preferred by most consumers around the world.

Deposition technologies to deliver after-wash moisturizing skin feel are widely described in various patents. Among these are included U.S. Pat. No. 5,716,920 to Wayne et al., WO 96/02224 A1 (assigned to Unilever), WO 96/17591 (assigned to Procter & Gamble), U.S. Pat. No. 6,066,608 to Glenn, Jr., U.S. Pat. No. 5,308,526 to Dias et al. and EP 0,648,111 B1 to Torres et al. In order to achieve the desirable after-wash skin benefits noted in these patents, the particle size, as described in the patents, has to be large than 20 micrometers.

In applicants copending application to Tsaur, filed on same date as the subject application, it has been found that the selection of the depositing moisturizing agents can be used to provide moisturizing liquids with soap-like rinsing attributes (e.g., as defined by "draggy" feel after certain number of counts). Specifically, by depositing large (e.g., 20–5000 micrometers), viscous (e.g., higher than 3000 cps at 30° C. at 1.0 $S^{-1}$) drops of a blend of hydrophobic polymer and emollient oils, the desired skin-feel is obtained. Preferred hydrophobic polymers include high MW (i.e., MW >900, preferably >1000) $C_2$–$C_{10}$ polyalkenes (e.g., polybutenes) and preferred oils which are mixable with the hydrophobic polymers include mineral oil, petrolatum, or triglycerides.

The use of hydrophobic polymers (e.g., polybutene) in shampoo and PW liquid compositions is not new as seen, for example, from U.S. Pat. No. 5,441,730 to Gough et al. and U.S. Pat. No. 5,580,550 to Gough et al.

WO 99109948 and WO 99/09950 (both assigned to Procter & Gamble) both disclose compositions in which polybutenes of MW 600 to about 1000 are used to enhance rinsability. Among the long, long recitation of optional ingredients which may be used is included hydrocarbons such as mineral oils and petrolatum (see WO 99109950 at page 27, line 16).

There is absolutely no teaching or suggestion in these references of the criticalities of the invention, e.g., specific selection of polymers which must have MW >900, preferably greater than 1000; using these necessarily in combination with oils of defined viscosity to obtain defined benefits; using critical size polymer/oil mixtures; and ensuring no more than certain level (less than 0.5%, preferably less than 0.3%) cationic is used (contrast with, for example, page 19, lines 12–13 of WO 99/09950 where cationic can be used up to levels as high as 3%).

U.S. Pat. No. 5,854,293 to Glenn, Jr. discloses liquid PW compositions containing large drop lipophilic moisturizing agent which agent may be a blend of petrolatum and polybutenes (column 3, lines 43–47).

Again, there is no recognition that polymers must be of certain size and certain molecular weight (e.g., higher than 900), that no more than certain amount of cationic may be used (contrast with column 5, lines 44–45) or that very specific criticalities will yield compositions which rinse well and provide "draggy" feel.

Finally, U.S. Pat. No. 5,869,070 to Dixon et al. disclose personal cleansing compositions containing skin moisturizing agent which is selected from the group consisting of petrolatum, hydrogenated polybutene and mixtures thereof, where ratio of petrolatum to polybetaine is 3:1 to 5:1. The composition also comprises 0.5 to 1.0 part polyquaternium 10 and 1 to 2.5 parts sodium polyacrylate. There is no recognition that, in process of making, specific criticalities, e.g., less than 0.5% cationic, must be met to achieve "draggy" feel as defined.

In general, the difficulty in preparing liquid cleansers having the desired large droplets of hydrophobic skin benefit agents (i.e., >20 micrometers) is recognized in patents such as U.S. Pat. No. 5,716,920 to Glenn, Jr. et al. Specifically, the large oil droplets tend to be destroyed during mixing, especially when the liquid cleanser is viscous and contains high level of surfactants.

Several methods have been described in the patent literature to make liquid cleansers containing large oil droplets. U.S. Pat. No. 5,716,920 discloses a complex coacervation method to encapsulate and to protect large oil droplets during the processing of liquid cleanser. U.S. Pat. No. 5,308,526 to Dias, WOP 96/17591 to Kacher and EP 0,648, 111 B1 to Torres teach a single vessel process to make large oil droplet by mixing the hydrophobic skin benefit agent directly with the liquid cleanser in a mixing vessel at low shear mixing condition. WO 96/02224 to Jobling et al. and WO 96117591 described in- line static mixer for the processing of large oil droplets.

Unexpectedly, it has been found that liquid cleanser containing large oil droplets can be prepared simply by passing the cleanser through a screen or screens having specific size of openings. The size of oil droplets can be easily controlled by the number of screens and the size of the opening on the screen. The present invention relates to an in-line screen process for making liquid compositions containing large oil droplet with size in the range of 20 to 5000 micrometers.

BRIEF DESCRIPTION OF INVENTION

In a copending application, applicants have found that use of specific polymers (i.e., minimum tackiness defined by minimum viscosity) in combination with specific oils provide not only moisturizing benefits, but also can provide good rinsability and soap-like "draggy" feel desirable by many consumers. To provide perceivable wet and dry skin sensation, the drop size of polymer/oil blend in the liquid cleanser has to be larger than 20 microns, preferably larger than 50 microns. The subject invention provides for a process to make liquid cleanser containing droplets of oil, generally, or of the oil/polymer blend of the copending application with size larger than 20 micron, preferably larger than 50 micron using an in-line screen. To achieve large drop size, the viscosity of the oil or oil/polymer blend has to be higher than 3000 centistokes, preferably higher than 10,000 centistokes at 30° C. at 1.0 $S^{-1}$.

More specifically, the subject invention comprises a process for making a personal cleansing composition having desirable rinsing and moisturization properties (and having soap-like rinsability according to separate copending application) wherein said process comprises:

(1) preparing a structured liquid cleanser (i.e., a liquid able to suspend 20 micron oil droplets without phase separation at R.T. for over 3 months) containing 5 to 35% by wt. of a surfactant composition having a viscosity higher than 200 stokes (e.g., 20,000 centistokes) measured at $0.1\ S^{-1}$ at 30° C.;

(2) separately mixing oil and optionally polymer to form oil or oil/polymer mixture with viscosity higher than 3,000 centistokes, preferably higher than 10,000 centistokes at 30° C. at $1.0\ S^{-1}$;

(3) mixing or injecting 1 to 30% by wt. of oil or oil/polymer blend into 70 to 99% by wt. of said structured liquid cleanser to form oil or oil/polymer droplets having size larger than 100 micrometers, preferably higher than 200 micrometers; and (4) passing the composition of step 3 through a screen having opening larger than 30 micrometers, preferably greater than 50 micrometers to make the final products; wherein size of particle in step (3) is larger than size of opening of screen used in step (4).

The prepared final composition is stable at room temperature for over 3 months without visible physical separation.

DETAILED DESCRIPTION OF INVENTION

The present invention relates to a process for making personal cleansing compositions comprising large droplets of oil or oil/polymer blend which are used to provide soap-like rinsability and/or after-wash skin benefits. More specifically, the invention relates to a process of providing desirable moisturizing properties and/or soap-like rinsability by carefully (a) selecting oil and/or oil/polymer blend; (b) formulating structured surfactant system; and (c) mixing or injecting oil or oil/polymer mixture into said structured liquid followed by passing through in-line screen (e.g., a screen connected to a vessel or tank used in process).

More specifically, the process of the invention comprises a process for making personal cleansing composition having desired moisturization wherein said process comprises:

(1) preparing a structured liquid cleanser (i.e., one able to support oil droplets or oil/polymer droplets having size of greater than 20 microns; at room temperature over 3 months) containing 5% to 35% by wt. of a surfactant composition having viscosity greater than 200 stokes at $0.1\ S^{-1}$ (surfactant may be anionic, nonionic, amphoteric/zwitterionic, cationic or mixtures);

(2) separately mixing oil or oil/polymer (such as oil/polymer disclosed in copending application filed same date) to form oil or oil/polymer mixture having viscosity higher than 3000 centistokes measured at 30° C. at $1.0\ S^{-1}$;

(3) mixing or injecting 1% to 30% by wt. oil or oil/polymer blend into 70 to 99% of said structured liquid cleanser to form oil or oil/polymer droplets having size larger than 100, preferably greater than 200 micrometers; and (4) passing composition of step 3, in an in-line process, through a screen or screens having opening larger than 30 micrometers, preferably larger than 50 micrometers to form final product;
wherein size of particle in Step 3 is larger than size of opening of screen(s) in Step 4

Each of the various components of the composition made by the process of the invention is described in more detail below.

SURFACTANT SYSTEM

The composition made by the process of the invention comprises a structured liquid composition containing 5 to 35%, preferably 8 to 30% by wt. surfactant composition.

The surfactants in the composition may be anionic, nonionic, amphoteric/zwitterionic, cationic or mixtures thereof as long as the compositions retain minimal lathering profile. That is, the surfactant or mixture combined should have an equilibrium surface tension between 15 and 50 dynes/cm, preferably 20–40 dyneslcm as measured at CMC at 25° C. Some surfactant mixes can have tension lower than those of individual components.

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGES); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

These differ from ether sulfates of the invention in that they are not branched.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$R^4O_2CCH_2CH(SO_3M)CO_2M;$ amido-MEA sulfosuccinates of the formula

$R^4CONHCH_2CH_2O_2CCH_2CH(SO_3M)CO_2M$ wherein $R^4$ ranges from $C_8$–$C_{22}$ alkyl and M is a solubilizing cation; amido-MIPA sulfosuccinates of formula

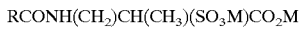
$RCONH(CH_2)CH(CH_3)(SO_3M)CO_2M$ where M is as defined above.

Also included are the alkoxylated citrate sulfosuccinates; and alkoxylated sulfosuccinates such as the following:

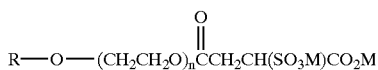
$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$R—(CH_2CH_2O)_nCO_2M$ wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_8$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Iardi et al., U.S. Pat. No. 5,393,466, hereby incorporated by reference into the subject application. This compound has the general formula:

In general the "additional" anionic component will comprise from about 1 to 20% by weight of the composition, preferably 2 to 15%, most preferably 5 to 12% by weight of the composition. It may also include a C8 to C14 unbranched fatty acid hydrocarbon (e.g., lauric acid, palmitic acid, capric, etc.) in levels of 10–50%, preferably 10–30% of total surfactant. Of course, soap may comprise less than 5% or may be absent altogether.

ZWITTERIONIC AND AMPHOTERIC SURFACTANTS

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

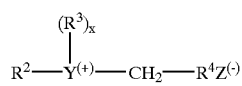

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of for example nitrogen, atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

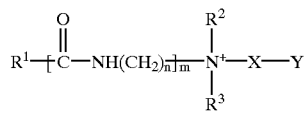

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

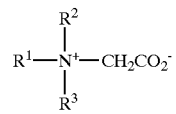

and amido betaines of formula:

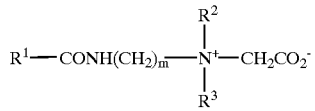

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

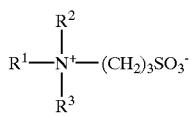

or

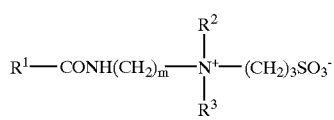

where m is 2 or 3, or variants of these in which $—(CH_2)_3SO^-_3$ is replaced by

In these formulae $R^1$, $R^2$ and $R^3$ are as discussed previously.

Amphoacetates and diamphoacetates are also intended to be covered in possible zwitterionic and/or amphoteric compounds which may be used.

The surfactant system may also optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_8$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

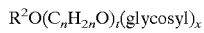

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic generally comprises 0 to 10% by wt. of the composition.

Cationic synthetic surfactant should not serve as the sole surfactant in this product, but can be used as a co-surfactant at a lower level of from about 0.5% to about 6% by weight. The more preferred types of cationic surfactant are selected from the group consisting of: alkyl Timonium chloride and methosulfate, and dialkyldimonnium chloride and methyl sulphate, and alkyl alkonium chloride and methyl sulphate and mixtures thereof. These surfactants contain $C_{12}$ to $C_{24}$ carbon atoms per alkyl chain. The most preferred cationic is selected from the group consisting of stearylalkonium chloride, stearyltrimonium chloride. Di-stearyl-dimonium chloride, and mixtures thereof.

POLYMER/OIL BLEND

If the oil is combined with polymer (as in applicants application filed same date for producing draggy or very draggy wet feel as defined by in-shower rinsability evaluation method), the polymer/oil blend used comprises 1 to 30%, preferably 3 to 20% by wt. of composition and the blend itself comprises 10 to 90%, preferably 20 to. 80% polymer and about 20 to 90%, preferably 30 to 80% hydrophobic oil.

The polymer in such blend may be any oil mixable hydrophobic linear or branched polymer having molecular weight greater than 900, preferably greater than 1000 daltons, a viscosity greater than 10,000 centistokes at 30° C. and 1 $S^{-1}$ and a tackiness of greater than 100 grams as measured by tackiness test. Preferred polymers may be hydrogenated or non-hydrogenated polymer of alkylene or isoalkylene such as polybutene, polyisobutene, polybutadiene or polyisoprene, polyalphaolefin, polyester, and polyacrylate and its copolymers. Most preferred polymers are commercially available polymers such as Indopol H1500®, Indopol H1900®, and Panalane H300E® from Amoco, Aquapel 32S®, Aquapel 15L®, and Puresyn ME2500® from Mobil.

The oil may be any emollient oils mixable with the said hydrophobic polymers and provide properties noted below after blended with the hydrophobic polymer. The preferred emollient oils may be petrolatum, mineral oil, triglyceride oils such as sunflower seed oil, soybean oil or caster oil, and esters such as isopropyl palmitate.

As noted, oil may be used alone for purposes of this process.

If used as blend, the oil is mixed with oil-mixable polymer at ratio of 9 to 1 to 1 to 8 to provide a blend which together has viscosity higher than 3000 centistoke at 30° C. at $1S^{-1}$.

The blend is characterized in that the tackiness value of the blend is in the range of 30 to 400 grams, preferably 50 to 300 grams, as measured by the TA texture analyzer; and that average particle size as existed in the liquid cleanser is in range of 20 to 5000 micrometers, preferably 50 to 1000 micrometers.

According to the process of the applicants application filed on same date, it was surprisingly found that the wet skin feel is dependent on both the molecular weight of the oil-mixable polymer (e.g., polyalkalene) and the ratio of polymer to oil. The process manipulates these factors and minimizes amount of cationic to provide desirable moisture and soap-like rinsability.

POLYMERIC STABILIZER

An optional component of the compositions made by the process of the invention is organic, inorganic or polymeric stabilizer. Specifically, the compositions may comprise 0 to 10% by wt. of an organic, inorganic or polymeric stabilizer which provides physical stability of the large oil droplets, (droplets of oil or polymer/oil blend) in the surfactant composition at 40° C. for over four weeks.

Generally the organic polymeric stabilizers used in the process include, but are not limited to, any of several long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof. Another example of suspending agent useful in the present invention include the alkanolamides having from about 14 to about 22 carton atoms. Preferred alkanolamides are stearic monoethanolamide, stearic diethanolamide stearic monoisopropanolamide, stearic monoethanolamide stearate and mixtures thereof. Still another example of a suspending agent useful in the present invention include the long chain fatty acid esters such as stearyl stearate, stearyl palmitate, palmityl palmitate, trihydroxystearylglycerol and tristearylglycerol. Still another example of a suitable suspending agent useful in the present invention include the long chain amine oxides having from about 14 to about 22 carbon atoms. Preferred amine oxides are hexadecyldimethylamine oxide and octadecyidimethylamide oxide.

Example of a suitable polymeric suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum. Of all the above described types of suspending agents, preferred compounds include the long chain glycol ester and the carbohydrate gums. Other stabilizers which may be used are set forth in U.S. Pat. No. 5,854,293 to Glenn, Jr. at column 4, line 36 to column 6, line 65. This reference is hereby incorporated by reference into the subject application.

The suspending agent or mixtures of agent may be present from about 0 to 10% of the composition.

CATIONIC POLYMER

The invention may also contain cationic polymer.

Suitable cationic polymers which may be used include Guar hydroxypropyltrimonium chloride, Quaternium-19, -23, -40, -57, poly(dimethyldiallylammonium chloride), poly (dimethyl butenyl ammonium chloride)-, w-bis (triethanolammonium chloride), poly (dipropyidiallylammonium chloride), poly (methyl-beta propaniodiallylammonium chloride), poly (diallylpiperidinium chloride), poly (vinyl pyridinium chloride), quaternised poly (vinyl alcohol),quaternized poly (dimethylaminoethylmethacrylate) and mixtures thereof.

Finally, it is another criticality of the process of the invention that the final composition made by the process provides a draggy or very draggy wet skin feel after fewer than 8 rubbing cycles as determined by in-shower evaluation method if soap-like clean rinsing sensation is preferred.

Compositions made by the process of the invention may suspend oil/emollient particles. The following oil/emollients may optionally be suspended in the compositions.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: acetylated lanolin alcohols, lanolin, lard, mink oil and tallow.

Other examples of oil/emollients include mineral oil, petrolatum, silicone oil such as dimethyl polysiloxane, lauryl and myristyl lactate.

The emollient/oil is generally used in an amount from about 1 to 30%, preferably 5 to 20% by wt. of the composition. Generally, it should comprise no more than 30% of the composition.

In addition, the compositions of the invention may include optional ingredients as follows:

Organic solvents, such as ethanol; auxiliary thickeners, sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Another optional ingredient which may be added are the deflocculating polymers such as are taught in U.S. Pat. No. 5,147,576 to Montague, hereby incorporated by reference.

Other ingredients which may be included are exfoliants such as polyoxyethylene beads, walnut sheets and apricot seeds Compositions of the invention are "structured" by which is meant they are capable of suspending oil particles with 20 microns for over 3 months without phase separation. Further, they have viscosity higher than 200 stokes (20,000 centistokes), preferably greater than 400 stokes measured at $0.1\ S^{-1}$ at 30° C.

PARTICLE SIZE OF OIL OR OIL/POLYMER BLEND AND ITS PROCESS

Particle size of the oil or oil/polymer blend have a significant effect on cleanser rinsability and the after-wash moisturizing skin feel. In general the larger the droplet size the more efficient the oil/polymer blend to increase cleanser's rinsability and after-wash conditioning agent. To work as an efficient rinsing aid or skin conditioning agent, the droplet size of the oil or blend should be larger than 20 microns, preferably larger than 50 microns. The upper limit of the oil or oil/polymer blend droplets can be as large as 5000 microns, preferably 1000 microns depending on the cleanser's suspension properties and also the tackiness of the oil or oil/polymer blends. For oil or oil/polymer blend with tackiness higher than 200 grams, the upper limit of the particle size is preferably less than 1000 microns to prevent undesirable sticky patch wet-skin feel. For good rinsability and good in-use sensory properties, the weight average particle size of oil or oil/polymer blend should be in the range of 20 to 5000 microns, preferably 50 to 1000 microns, most preferably 100 to 400 microns.

Liquid cleansers containing oil or oil/polymer droplets with size larger than 20 microns can be accomplished either in a batch wise process or in a continuous process depending on how the oil or oil/polymer blend and the surfactant solution are mixed. A batch process such as an overhead mixer or a floatation machine, or a continuous process such as a two fluid co-extrusion nozzle, an in-line injector, an in-line static mixer can be used to make the large droplet of oil or oil/polymer blend with the desired particle size. The size of the oil/polymer blend can be manipulated by changing the mixing speed, mixing temperature, mixing time, viscosity of the surfactant solution or oil/polymer blend, and the mixing device. In general, by reducing the mixing time, decreasing the mixing speed, lowering the viscosity of the surfactant solution, increasing the viscosity of the oil/polymer blend, or using a mixing device that produces less shear force during mixing, one can produce larger size. However, it is difficult to control the size and the uniformity of the oil or oil/polymer droplet using these methods.

The most preferred process (i.e., that of invention) to make large droplet of oil or oil/polymer blend with uniform controllable drop size is a low shear mixing in-line screen process described as following. Oil (and polymer) are/is mixed either at ambient or elevated temperature to form a uniform mixture (oil mixed separately than structured surfactant containing composition). The oil or oil/polymer blend is then mixed or injected into a well structured surfactant solution (e.g., a surfactant solution capable of suspending large oil/polymer particles) at low mixing condition (e.g., low shear) to form oil or oil/polymer particles with a size from several hundred microns to several millimeters. Generally 1 to 30%, preferably 3 to 25% by wt. of oil/polymer blend are mixed into 70 to 99%, preferably 75 to 97% cleanser base. The oil/polymer mixture has viscosity higher than 3000 centistokes, preferably higher than 10,000 centistokes, measured at 30° C. at $1.0 \, S^{-1}$.

The large oil or oil/polymer particles are then broken to particles of desirable size by passing through in-line screen. Particle size can be controlled easily by the opening size and the number of screens. For example screens have size larger than 30, preferably larger than 50 micrometers, even more preferably higher than 100 micrometers. There may be one or more in-line screens and each screen may have openings of varying size. Further, oil/polymer particles can be passed through screens as many times as desirable.

Size and shape of the entire screen do not matter for purpose of the invention, only the size of the screen openings.

The invention will now be described in greater detail by way of the following non-limiting examples. The examples are for illustrative purposes only and not intended to limit the invention in any way.

Except in the operating and comparative examples, or where otherwise explicitly indicated, all number in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

METHODOLOGY

TACKINESS MEASUREMENT

A Texture Analyzer (TA-XT2 from Textile Technologies Corp.) equipped with TA-57R probe was used for tackiness measurement. 0.1 to 0.15 cc of materials was injected onto a glass plate. The TA was set so that the probe passes through the liquid and presses it against the glass plate. Once the probe attains a 0.5 grams trigger force, the Texture Expert software begins taking measurements of the force as a function of time. The probe continues to compress the sample at the set applied force. The TA will retract once the set time delay has elapsed. The TA measures the force as it retracts from the surface. The maximum force required to pull the probe away from a material is recorded as the tackiness value of the material and is used to compare the relative tackiness of different material. A tackier material has a higher tackiness value. Three measurements were taken consecutively and the average was calculated and shown in Table 2 for some polymers and oil/polymer blends. The TA settings used in the measurement is shown in the Table 1.

TABLE 1

TA Setting for the Tackiness Measurement

Hold until time

| | |
|---|---|
| Pre-speed: | 5 mm/s |
| Test-speed: | 5 mm/s |
| Post-speed: | 10 mm/s |
| Applied force: | 10 g |
| Set time | 20 s |
| Trigger type: | Auto |
| Trigger force: | 0.5 g |
| Acquisition rate: | 200 PPS |
| Probe: | TA-57R |
| Load cell: | 5–0.1 |

TABLE 2

Tackiness Value of Polymers and Polymer/Oil Blends

Oil/Polymer Composition

| Wt % of Emollient Oil | Wt % of Polymer | Tackiness (grams) |
|---|---|---|
| | 100% Indopol H25 | 39.2 |
| | 100% Indopol H40 | 70.6 |
| | 100% Indopol H100 | 134.0 |
| | 100% Indopol H300 | 258.2 |
| | 100% Indopol H1500 | Overload |
| | 100% Aquapel 32s | Overload |
| 33.3% mineral oil | 66.7% Indopol H100 | 43.1 |
| 50% mineral oil | 50% Indopol 1 H100 | 24.9 |
| 33.3% mineral oil | 66.7% Indopol H300 | 77.3 |
| 50% mineral oil | 50% Indopol H300 | 37.9 |
| 66.7% mineral oil | 33.3% Indopol H300 | 17.8 |
| 50% mineral oil | 50% Indopol H1500 | 71.3 |
| 75% mineral oil | 25% Indopol H1500 | 16.8 |
| 50% mineral oil | 50% Aquapel 32s | 181.3 |
| 66.7% mineral oil | 33.3% Aquapel 32s | 90.6 |
| 75% mineral oil | 25% Aquapel 32s | 61.9 |
| 2 Sunflower Oil | 33.3% Aquapel 32s | 41.2 |
| 1 Soybean Oil | 50% Aquapel 32s | 61.5 |
| 66.7% Indopol L14 | 33.3% Aquapel 32s | 57.6 |
| 66.7% Indopol L14E | 33.3% H1500 | 16.3 |
| 90% petrolatum | 10% Indopol H300 | 56.2 |
| 75% petrolatum | 25% Indopol H300 | 66.9 |
| 66.7% petrolatum | 33.3% Indopol H300 | 72.6 |
| 50% petrolatum | 50% Indopol H300 | 110.6 |
| 33.3% petrolatum | 66.7% Indopol H300 | 135.2 |
| 33.3% petrolatum | 66.7% Indopol H40 | 42.3 |

TABLE 2-continued

Tackiness Value of Polymers and Polymer/Oil Blends

| Oil/Polymer Composition | | |
|---|---|---|
| Wt % of Emollient Oil | Wt % of Polymer | Tackiness (grams) |
| 75% petrolatum | 25% Indopol H100 | 61.3 |
| 75% petrolatum | 25% Aquapel 32S | 191.9 |
| 90% petrolatum | 10% Aquapel 32s | 87.3 |
| 75% petrolatum | 25% Indopol H40 | 43.4 |
| 80% petrolatum | 20% Indopol H1500 | 107.8 |
| 75% petrolatum | 25% Indopol H25 | 39 |
| 50% petrolatum | 50% Aquapel 32S | 332.7 |
| 95% petrolatum | 5% Aquapel 32S | 66.4 |

For good rinsability, polymers should have a tackiness higher than 100 grams and the mixture of polymer and oil is preferably has a tackiness value higher than 20 grams, more preferably higher than 30 grams.

In-Shower Rinsability Evaluation Method

Method described below was used to evaluate rinsability of personal cleanser in the shower. A soap-based personal washing liquid such as Lux from Taiwan has a very drag wet skin feel after 3 to 4 rubbing cycle during rinsing. A synthetic-based liquid such as Taiwan Dove body wash has a slightly drag wet skin feel after 8 to 10 rinsing cycles. A cationic polymer-containing shower liquid such as U.S. Dove has a very slippery wet-skin feel after 10 to 12 rubbing cycles.

1. First wet the body under running water.
2. Stay away from the running water, apply and lather about 5 cc of liquid all over the body.
3. Stand in front of the shower and start to rinse while rubbing the chest up and down with both hands at a speed of about 1.5 to 1.8 seconds per cycle.
4. Count the times of rubbing cycle to perceive a drag feel, and determine the drag feel 2 to 3 more cycles after perceiving the initial drag. Degree of drag is rated as following

| | |
|---|---|
| Very Draggy | There is great resistance to prevent hands moving along the skin, both hand feel like they are stuck on the skin |
| Draggy | There is resistance to prevent hand moving on the skin. Hands can move through the skin with some stick and slip feel (jumpy). |
| Slight Draggy | Hand can move freely on the skin with some resistance |
| Slippery | Hands move smoothly on the wet skin with no resistance at all after 10 rubbing cycles |

EXAMPLES

Example 1

Effect of Oil-Mixable Polymer on Cleanser's Rinsability (In Absence of Oil With Which to Form Polymer/Oil Blend)

TABLE 3

| | Effect of Polymer | | | | | |
|---|---|---|---|---|---|---|
| Example # | 1A | 1B | 1C | 1D | 1E | Control |
| Lauric acid | 4.23 | 4.23 | 4.23 | 4.23 | 4.23 | 4.5 |
| Na Lauryl-amphoacetate | 4.94 | 4.94 | 4.94 | 4.94 | 4.94 | 5.25 |
| Na Lauryl-sulfosuccinate | 4.94 | 4.94 | 4.94 | 4.94 | 4.94 | 5.25 |
| Triethanol amine | 3.1 | 3.1 | 3.1 | 3.1 | 3.1 | 3.3 |
| Xanthan Gum, Keltro CRD | 1.13 | 1.13 | 1.13 | 1.13 | 1.13 | 1.2 |
| Glycerine | 9.4 | 9.4 | 9.4 | 9.4 | 9.4 | 10 |
| Perfume | 0.47 | 0.47 | 0.47 | 0.47 | 0.47 | 0.5 |
| Glydant plus | 0.19 | 0.19 | 0.19 | 0.19 | 0.19 | 0.2 |
| Polybutene Indopol L20 | 6 | — | — | — | — | — |
| Polybutene Indopol H40 | — | 6 | — | — | — | — |
| Polybutene Indopol H100 | — | — | 6 | — | — | — |
| Polybutene Indopol H300 | — | — | — | 6 | — | — |
| Polybutene Indopol H1500 | — | — | — | — | 6 | — |
| Counts to detect drag feel | 9 | 6–7 | 3–4 | 3–4 | 3–4 | 8–9 |
| Degree of drag | SD | D–SD | VD (sticky) | VD (sticky) | VD (sticky) | SD |

Examples given in Table 3 above show effect of oil-mixable polymer with different tackiness value on cleanser's rinsability using the In-Shower Rinsability Evaluation Method described earlier. First a xanthan-structured cleanser containing 15 wt % of surfactants was prepared and used as a control for comparison. Effect of polymer on cleanser's rinsability was evaluated by adding 6 wt % of polybutene to 94 wt % of the control. The polymer-containing samples were prepared as follow. Six parts of polybutene was first injected into 94 parts of the pre-prepared xantham-structured liquid to form large lumps of polymers. The polymer/cleanser mixture was then passed through a screen with 500-micrometer opening twice to form large polymer droplets with size in the range of several micrometers up to several hundreds micrometers. The weight average particle size of these samples is larger than 50 micrometers.

It should be noted that the droplets can be passed through screen 1 time or 2 times or more depending on desired size (more times through vessel equals smaller particles).

In addition, size can be controlled simply by screen size, or for example by using different screens of varying size.

Compared to the control (no polybutene), the results showed that rinsability can be enhanced by adding polybutene to the cleanser. To achieve good rinsability (less than 5 to 6 counts and having drag or very drag wet-skin feel) polymers with high tackiness value (more than 100 grams determined by the Texture Analyzer method) are required. However, despite the effectiveness to enhance cleanser's rinsability, polymers with a high tackiness value have a very undesirable sensory property during rinsing (see 1C, 1D &

1E). It gives a very sticky gluey wet-skin feel especially on the hairy part of the body. This tacky gluey feel make them unsuitable for the applications of personal cleansing products. In short, the compositions are rinsable, but feel sticky.

This example also shows process of invention wherein large size droplets are made by passing cleanser through screen or screens.

Example 2

Effect of Oil/Polymer Blend on Rinsability

TABLE 4

Polymer/Oil Blend on Rinsability

| Example # | 2A | 2B | 2C | 2D | 2E | 2F | 2G | Control |
|---|---|---|---|---|---|---|---|---|
| Lauric acid | 4.23 | 4.23 | 4.23 | 4.23 | 4.05 | 4.05 | 4.23 | 4.5 |
| Na Laurylamphoacetate | 4.94 | 4.94 | 4.94 | 4.94 | 4.73 | 4.73 | 4.94 | 5.25 |
| Na Laurylsulfosuccinate | 4.94 | 4.94 | 4.94 | 4.94 | 4.73 | 4.73 | 4.94 | 5.25 |
| Triethanol amine | 3.1 | 3.1 | 3.1 | 3.1 | 3.0 | 3.0 | 3.1 | 3.3 |
| Xanthan Gum, Keltro CRD | 1.13 | 1.13 | 1.13 | 1.13 | 1.1 | 1.1 | 1.13 | 1.2 |
| Glycerine | 9.4 | 9.4 | 9.4 | 9.4 | 9 | 9 | 9.4 | 10 |
| Perfume | 0.47 | 0.47 | 0.47 | 0.47 | 0.45 | 0.45 | 0.47 | 0.5 |
| Glydant plus | 0.19 | 0.19 | 0.19 | 0.19 | 0.18 | 0.18 | 0.19 | 0.2 |
| Polybutene Indopol H40* | 3 | — | — | — | — | — | — | — |
| Polybutene Indopol H100* | — | 3 | — | — | — | — | — | — |
| Polybutene Indopol H300* | — | — | 3 | — | — | — | — | — |
| Aquapel 32S* | — | — | — | 3 | 5 | 3.3 | 3 | — |
| Mineral oil* | 3 | 3 | 3 | 3 | — | — | — | — |
| Sunflower oil* | — | — | — | — | — | 6.7 | — | — |
| Soybean oil* | — | — | — | — | 5 | — | — | — |
| Polybutene Panalane L14E* | — | — | — | — | — | — | 3 | — |
| DI Water | To 100 | To 100 | To 100 | To 100 | To 100 | To 100 | To 100 | To 100 |
| Counts to detect drag feel | 8 | 4–5 | 3–4 | 3–4 | 3–4 | 5–6 | 3–4 | 8–9 |
| Degree of drag | SD | D | VD | VD | VD | D | VD | SD |

*polymer and oil were premixed to form uniform mixture before adding to the liquid.

Same procedure described in Example 1 was used to prepare samples shown in Table 4. Polybutene and oil were mixed at 60° C. for about 20 to 30 minutes to form a uniform mixture. The polymer/oil mixture was cooled to room temperature before adding into the xanthan-structured liquid (the Control sample) and passing through a screen with 500-micrometer opening. The rinsability result shows that cleanser's rinsability can be enhanced (i.e., lower number of counts before it is draggy to very draggy) using polymer/oil blends with right material properties. For good rinsability, the tackiness value of the oil/polymer blend measured by Texture Analyzer, the oil/polymer blend is preferably higher than 20 grams, more preferably higher than 30 grams. Oil/polymer blend with higher tackiness gives a better rinsability. Sticky gluey wet-skin feel problem associated with these polymers can be eliminated by mixing the polymer with emollient oil even for the blends with a rinsability same as a soap-based liquid (3 to 4 counts with very drag wet-skin feel).

Example 3

Effect of Polymer/Oil Ratio on Rinsability

TABLE 5

| Example # | 3A | 3B | 3C | 3D |
|---|---|---|---|---|
| Lauric acid | 4.23 | 4.23 | 4.23 | 4.23 |
| Na Laurylamphoacetate | 4.94 | 4.94 | 4.94 | 4.94 |
| Na Laurylsulfosuccinate | 4.94 | 4.94 | 4.94 | 4.94 |

TABLE 5-continued

| Example # | 3A | 3B | 3C | 3D |
|---|---|---|---|---|
| Triethanol amine | 3.1 | 3.1 | 3.1 | 3.1 |
| Xanthan Gum, Keltro CRD | 1.13 | 1.13 | 1.13 | 1.13 |
| Glycerine | 9.4 | 9.4 | 9.4 | 9.4 |
| Perfume | 0.47 | 0.47 | 0.47 | 0.47 |
| Glydant plus | 0.19 | 0.19 | 0.19 | 0.19 |
| Polybutene Indopol H300* | 4 | 3 | 2 | 1.5 |
| Mineral oil* | 2 | 3 | 4 | 4.5 |
| DI Water | To 100 | To 100 | To 100 | To 100 |
| Counts to detect drag feel | 3–4 | 3–4 | 4–5 | 4–5 |
| Degree of drag | VD (sticky) | VD | D–VD | D–VD |

*polymer and oil were premixed to form uniform mixture before adding to the liquid.

Examples in Table 5 shows that cleansers with very good rinsability without the undesirable tacky gluey wet-skin feel can be achieved using blends of oil with a polymer of high tackiness value. Using this approach cleanser with different rinsability can be formulated simply by varying the ratio of oil to polymer added into the cleanser.

Example 4

Effect of Polymer/Petrolatum Blend on Rinsability

TABLE 6

| Example # | 4A | 4B | 4C | 4D | 4E | 4F | 4G | Control |
|---|---|---|---|---|---|---|---|---|
| Lauric acid | 4.05 | 4.05 | 4.05 | 4.05 | 4.05 | 4.05 | 4.32 | 4.50 |
| Na Laurylamphoacetate | 4.73 | 4.73 | 4.73 | 4.73 | 4.73 | 4.73 | 5.04 | 5.25 |
| Na Laurylsulfosuccinate | 4.73 | 4.73 | 4.73 | 4.73 | 4.73 | 4.73 | 5.04 | 5.25 |
| Triethanol amine | 3.0 | 3.0 | 3.0 | 3.0 | 3.0 | 3.0 | 3.2 | 3.3 |
| Xanthan Gum Keltro CRD | 1.1 | 1.1 | 1.1 | 1.1 | 1.1 | 1.1 | 1.15 | 1.2 |
| Glycerine | 9 | 9 | 9 | 9 | 9 | 9 | 9.6 | 10 |
| Perfume | 0.45 | 0.45 | 0.45 | 0.45 | 0.45 | 0.45 | 0.48 | 0.50 |
| Glydant plus | 0.18 | 0.18 | 0.18 | 0.18 | 0.18 | 0.18 | 0.19 | 0.20 |
| Polybutene Indopol H40* | 2.5 | — | — | — | — | — | — | — |
| Polybutene Indopol H100* | — | 2.5 | — | — | — | — | — | — |
| Polybutene Indopol H300* | — | — | 2.5 | — | — | — | — | — |
| Polybutene Indopol H1500* | — | — | — | 2.5 | — | — | 2.0 | — |
| Polybutene Aquapel 32S* | — | — | — | — | 2.5 | 1.0 | — | — |
| Petrolatum (Penreco Snow) | 7.5 | 7.5 | 7.5 | 7.5 | 7.5 | 9.0 | 2.0 | — |
| DI Water | To 100 | To 100 | To 100 | To 100 | To 100 | To 100 | To 100 | To 100 |
| Counts to detect drag feel | 7–8 | 4–5 | 3–4 | 3–4 | 3–4 | 5–6 | 4–5 | 9–10 |
| Degree of drag | SD | VD-D | VD | VD | VD | VD-D | D-VD | SD |

*polymer and petrolatum were premixed to form uniform mixture before adding to the liquid.

Same procedure described in Example 1 was used to prepare examples shown in Table 6 for rinsability evaluation. These results demonstrated again that for good rinsability the oil-mixable polymer should have a tackiness value higher than 100 grams. Polymers with tackiness value lower than 100 grams are not efficient to provide good rinsability after being mixed with an emollient oil such as petrolatum. Very good rinsability without the undesirable tacky gluey wet-skin feel can be achieved using polymer/petrolatum blend with a tackiness value even higher than 150 grams.

Example 5

Effect of Surfactant Composition

TABLE 7

| Example # | Control 5A | 5A | Control 5B | 5B-1 | 5B-2 |
|---|---|---|---|---|---|
| Lauric acid | 3 | 2.7 | 0 | 0 | 0 |
| Triethanol amine | 2.2 | 1.98 | 0 | 0 | 0 |
| Na Laurylamphoacetate | 5 | 4.5 | 10 | 9 | 9 |
| Na Laurylsulfosuccinate | 0 | 0 | 0 | 0 | 0 |
| Na laureth(3) sulfate | 6 | 5.4 | 4 | 3.6 | 3.6 |
| Xanthan Gum Keltro CRD | 1.2 | 1.08 | 1.2 | 1.08 | 1.08 |
| Glycerine | 10 | 9 | 10 | 9 | 9 |
| Perfume | 0.5 | 0.45 | 0.5 | 0.45 | 0.45 |
| Glydant plus | 0.2 | 0.18 | 0.2 | 0.18 | 0.18 |
| Polybutene Indopol H300* | 0 | 2.5 | 0 | 2.5 | 4.0 |
| Petrolatum (Penreco Snow) | 0 | 7.5 | 0 | 7.5 | 6.0 |
| DI Water | To 100 | To 100 | To 100 | To 100 | To 100 |
| Counts to detect drag feel | 9–10 | 3 | >12 | 7–8 | 4–5 |
| Degree of drag feel | SD | VD | slippery | D | VD |

*polymer and petrolatum were premixed to form uniform mixture before adding to the liquid.

Samples were prepared same as those in example 1 using different surfactant composition. The results showed that for same oil/polymer blend the cleanser's rinsability depends on the surfactant composition of the liquid (Example 5A vs. 5B-1). Surfactant composition that is rinsed easier has a better rinsability after adding the oil/polymer blend. For same surfactant composition better rinsability can be achieved using oil/polymer blend with higher tackiness value (Example 5B-1 vs. 5B-2).

Example 6

Effect of Cationic Polymer

TABLE 8

| Example # | 6A | 6B | 6C | 6D | Control |
|---|---|---|---|---|---|
| Lauric acid | 5.64 | 5.64 | 5.64 | 5.64 | 6 |
| Triethanol amine | 2.82 | 2.82 | 2.82 | 2.82 | 3.0 |
| Na Laurylamphoacetate | 13.2 | 13.2 | 13.2 | 13.2 | 14 |
| Trihydroxystearin | 1.12 | 1.12 | 1.12 | 1.12 | 1.2 |
| Methocel 40-101 (Hydroxy propyl methycellulose) | 0.2 | 0.0 | 0.0 | 0.0 | 0.2 |
| Jaguar C13S (cationic guar) | 0.0 | 0.1 | 0.2 | 0.3 | 0.0 |
| Glycerine | 3.0 | 3.0 | 3.0 | 3.0 | 3.0 |
| Perfume | 0.5 | 0.5 | 0.5 | 0.5 | 0.5 |
| Glydant plus | 0.2 | 0.2 | 0.2 | 0.2 | 0.2 |
| Polybutene Indopol H1500 | 3 | 3 | 3 | 3 | 0 |
| Petrolatum (Penreco Snow) | 3 | 3 | 3 | 3 | 0 |
| DI Water | To 100 | To 100 | To 100 | To 100 | To 100 |
| Counts to detect drag feel | 4–5 | 4–5 | 5–7 | >12 | >12 |
| Degree of drag feel | VD | VD | D–VD | slippery | slippery |

Effect of cationic polymer on cleanser's rinsability is shown in these examples. Instead of using xantham-structured liquid, a sample containing 20 wt % of surfactant structured with 1.2 wt % of trihydroxystearin was used as the control for rinsability study. These examples showed that cationic polymer has an big effect on cleanser's rinsability. To maintain good rinsability using large droplets of oil/polymer blend the level of cationic polymer in the cleanser is lower than 0.5 wt %, preferably lower than 0.3 wt. %.

What is claimed is:

1. A process for making a personal cleansing composition having desirable moisturization properties wherein said process comprises:

(1) preparing a structured liquid cleanser, containing 5 to 35% by wt. of a surfactant composition and having a viscosity higher than 200 stokes measured at 0.1 $S^{-1}$ at 30° C.;

(2) separately mixing oil and optionally polymer to form oil or oil/polymer mixture with viscosity higher than 3,000 centistokes at 30° C. at 1.0 $S^{-1}$;

(3) mixing or injecting 1 to 30% by wt. of oil or oil/polymer blend into 70 to 99% by wt. of said structured liquid cleanser to form oil or oil/polymer droplets having size larger than 100 micrometers; and (4) passing the composition of step 3 through a screen having opening larger than 30 micrometers to make the final products; wherein size of particle in step (3) is larger than size of opening of screen used in step (4), wherein said structure liquid can suspend 20 micron oil droplets without phase separation at room temperature for over 3 months.

2. A process according to claim 1, wherein viscosity of structured liquid is higher than 400 stokes.

3. A process according to claim 1, wherein viscosity of oil/polymer mixture is higher than 10,000 centistokes at 30° C. at 1.0 $S^{-1}$.

4. A process according to claim 1, wherein 5 to 25% of oil/polymer is injected.

5. A process according to claim 1, wherein size of openings in screen is greater than 50 micrometers.

* * * * *